(12) United States Patent
Harandi et al.

(10) Patent No.: US 11,130,915 B2
(45) Date of Patent: *Sep. 28, 2021

(54) METHODS FOR METHANOL-TO-GASOLINE CONVERSION WITH FORWARDING METHANOL PROCESSING

(71) Applicant: ExxonMobil Research and Engineering Company, Annandale, NJ (US)

(72) Inventors: Mohsen N. Harandi, New Hope, PA (US); Suriyanarayanan Rajagopalan, Spring, TX (US); David W. Staubs, Brevard, NC (US); Terry E. Helton, Montgomery, TX (US); Mitch L. Hindman, Hamilton, VA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/903,252

(22) Filed: Jun. 16, 2020

(65) Prior Publication Data
US 2020/0399544 A1    Dec. 24, 2020

Related U.S. Application Data

(60) Provisional application No. 62/862,860, filed on Jun. 18, 2019.

(51) Int. Cl.
*C10G 3/00* (2006.01)
*B01D 3/00* (2006.01)
(Continued)

(52) U.S. Cl.
CPC ............ *C10G 3/49* (2013.01); *C07C 41/09* (2013.01); *C07C 41/42* (2013.01); *C10L 1/06* (2013.01);
(Continued)

(58) Field of Classification Search
None
See application file for complete search history.

(56) References Cited

U.S. PATENT DOCUMENTS 4,035,430 A * 7/1977 Dwyer ............... C10G 3/49
585/322
4,665,249 A    5/1987 Mao et al.
(Continued)

*Primary Examiner* — Philip Y Louie
(74) *Attorney, Agent, or Firm* — Liza Negron

(57) ABSTRACT

Methanol-to-gasoline (MTG) conversion may be performed with forward methanol processing. Methanol may be fed to a first reactor where it may be catalytically converted under dimethyl ether formation conditions in the presence of a first catalyst to form a product mixture comprising dimethyl ether (DME), methanol, and water. The DME may be separated from the methanol and the water and delivered to a second reactor. In the second reactor, the DME may be catalytically converted under MTG conversion conditions in the presence of a second catalyst to form a second product mixture comprising gasoline hydrocarbons and light hydrocarbon gas. The methanol and the water from the first reactor may be separated further to obtain substantially water-free methanol, which may be delivered to the second reactor. The separation of methanol from the water may be performed using the light hydrocarbon gas to effect stripping of the methanol.

19 Claims, 2 Drawing Sheets

(51) Int. Cl.
*C07C 41/09* (2006.01)
*C10L 1/06* (2006.01)
*C07C 41/42* (2006.01)

(52) U.S. Cl.
CPC ............... *C10L 2200/0423* (2013.01); *C10L 2200/0469* (2013.01); *C10L 2270/023* (2013.01)

(56) References Cited

U.S. PATENT DOCUMENTS

| | | | |
|---|---|---|---|
| 4,826,662 A * | 5/1989 | Mao | C07C 41/09 202/154 |
| 5,750,799 A * | 5/1998 | van Dijk | C07C 41/09 568/698 |
| 9,938,205 B2 | 4/2018 | Du et al. | |
| 2010/0240779 A1 * | 9/2010 | Nielsen | C10G 3/49 518/705 |
| 2015/0175898 A1 | 6/2015 | McCarthy et al. | |
| 2016/0102031 A1 | 4/2016 | Du et al. | |
| 2016/0178132 A1 | 6/2016 | Harandi et al. | |
| 2017/0121615 A1 | 5/2017 | Harandi et al. | |
| 2017/0137342 A1 | 5/2017 | Behkish et al. | |
| 2017/0137720 A1 | 5/2017 | Harandi et al. | |
| 2018/0170823 A1 * | 6/2018 | Rajagopalan | C10G 3/49 |

\* cited by examiner

METHODS FOR METHANOL-TO-GASOLINE CONVERSION WITH FORWARDING METHANOL PROCESSING

CROSS REFERENCE TO RELATED APPLICATIONS

This application claims priority to U. S. Provisional Application Ser. No. 62/862,860 filed Jun. 18, 2019, which is herein incorporated by reference in its entirety.

FIELD

The present disclosure relates to methanol-to-gasoline conversion methods.

BACKGROUND

During methanol-to-gasoline (MTG) conversion processes, an equilibrium mixture of methanol and dimethyl ether (DME) is contacted with a zeolite catalyst, such as ZSM-5, in the presence of light hydrocarbon recycle gas, under conditions effective to convert the equilibrium mixture into gasoline hydrocarbons. In typical MTG conversion processes, an MTG reactor (e.g., an axial-flow, packed-bed reactor) is directly fed the equilibrium mixture from a DME reactor that produces the equilibrium mixture in the presence of a suitable catalyst. The methanol feed to the DME reactor usually comprises about 7 mol. % water (about 4.1 wt. %), and the equilibrium mixture obtained following DME production usually comprises methanol, DME, and about 40 mol. % water (~25 wt. %), with the additional water resulting from dehydration of the methanol to form the DME. Process guidance usually suggests a maximum water content of 5 wt. % for the methanol feed provided to the DME reactor. After feeding the equilibrium mixture to the MTG reactor, a mixture of gasoline hydrocarbons and light hydrocarbon gas is obtained. The light hydrocarbon gas may be separated and recycled to the MTG reactor, primarily to aid in regulating the temperature therein.

The reaction that occurs in the MTG reactor is exothermic, and the catalyst undergoes two types of aging that contribute to a gradual loss of catalyst activity. The first type of aging is coke formation on the catalyst. The coke is a temporary deactivation agent that forms during the MTG reaction, and it may be removed during catalyst regeneration. The second type of aging is permanent deactivation resulting from dealumination of the zeolite catalyst. Introduction of water to the MTG reactor within the equilibrium mixture promotes the dealumination process, particularly at high temperatures. Since water is co-produced with DME, it is not usually feasible to control the amount of water introduced to the MTG reactor in conventional MTG conversion processes. Instead, conventional MTG conversion processes typically seek to control the reaction temperature as a means for limiting dealumination.

Lowering the MTG reaction temperature to limit dealumination is not without its consequences, however. The lower reaction temperature may decrease the reaction rate. Even more significantly, the production rate of durene (1,2,4,5-tetramethylbenzene) may increase substantially as the MTG reaction temperature decreases. Co-production of significant quantities of durene (>2 wt. %) with gasoline hydrocarbons can be especially problematic, since durene can crystallize above a threshold concentration in cold climates. As such, great care may be needed to ensure that on-specification gasoline hydrocarbons are obtained in conventional MTG conversion processes. If excessive durene formation occurs, a heavy gasoline treatment (HGT) unit may be used to isomerize the durene into a less problematic product. Although a heavy gasoline treatment may be effective to address durene formation, doing so may significantly add to the cost of performing a MTG process.

SUMMARY

In some embodiments, the present disclosure provides methods for methanol-to-gasoline conversion with forward methanol processing. The methods comprise: providing a feed comprising methanol to a first reactor; catalytically converting at least a portion of the feed in the first reactor under dimethyl ether formation conditions in the presence of a first catalyst to form a first product mixture comprising dimethyl ether (DME), methanol, and water; separating the first product mixture into a first fraction comprising the DME and a second fraction comprising the methanol and the water; providing the first fraction to a second reactor; catalytically converting at least a portion of the DME in the second reactor under methanol-to-gasoline (MTG) conversion conditions in the presence of a second catalyst to form a second product mixture comprising gasoline hydrocarbons and light hydrocarbon gas; separating the second fraction into substantially water-free methanol and an aqueous effluent; and delivering the substantially water-free methanol to the second reactor.

In some embodiments, the present disclosure provides methods for methanol-to-gasoline conversion with forward methanol processing coupled with use of a co-produced light hydrocarbon gas to effect separation of methanol. The methods comprise: providing a feed stream comprising methanol to a first reactor; catalytically converting at least a portion of the feed stream in the first reactor under dimethyl ether formation conditions in the presence of a first catalyst to form a first product mixture comprising DME, methanol, and water; delivering the first product mixture in a first stream from the first reactor to a first separation unit; separating the first product mixture in the first separation unit to obtain a first fraction comprising the DME and a second fraction comprising the methanol and the water; delivering the first fraction in a second stream to a second reactor; catalytically converting at least a portion of the DME in the second reactor under MTG conversion conditions in the presence of a second catalyst to form a second product mixture comprising gasoline hydrocarbons and light hydrocarbon gas; delivering the second fraction in a third stream to a second separation unit; delivering at least a first portion of the light hydrocarbon gas to the second separation unit; separating the second fraction in the second separation unit into substantially water-free methanol and an aqueous effluent using the light hydrocarbon gas to effect stripping; and delivering the substantially water-free methanol to the second reactor.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one of ordinary skill in the art and having the benefit of this disclosure.

DETAILED DESCRIPTION

Figure 1:
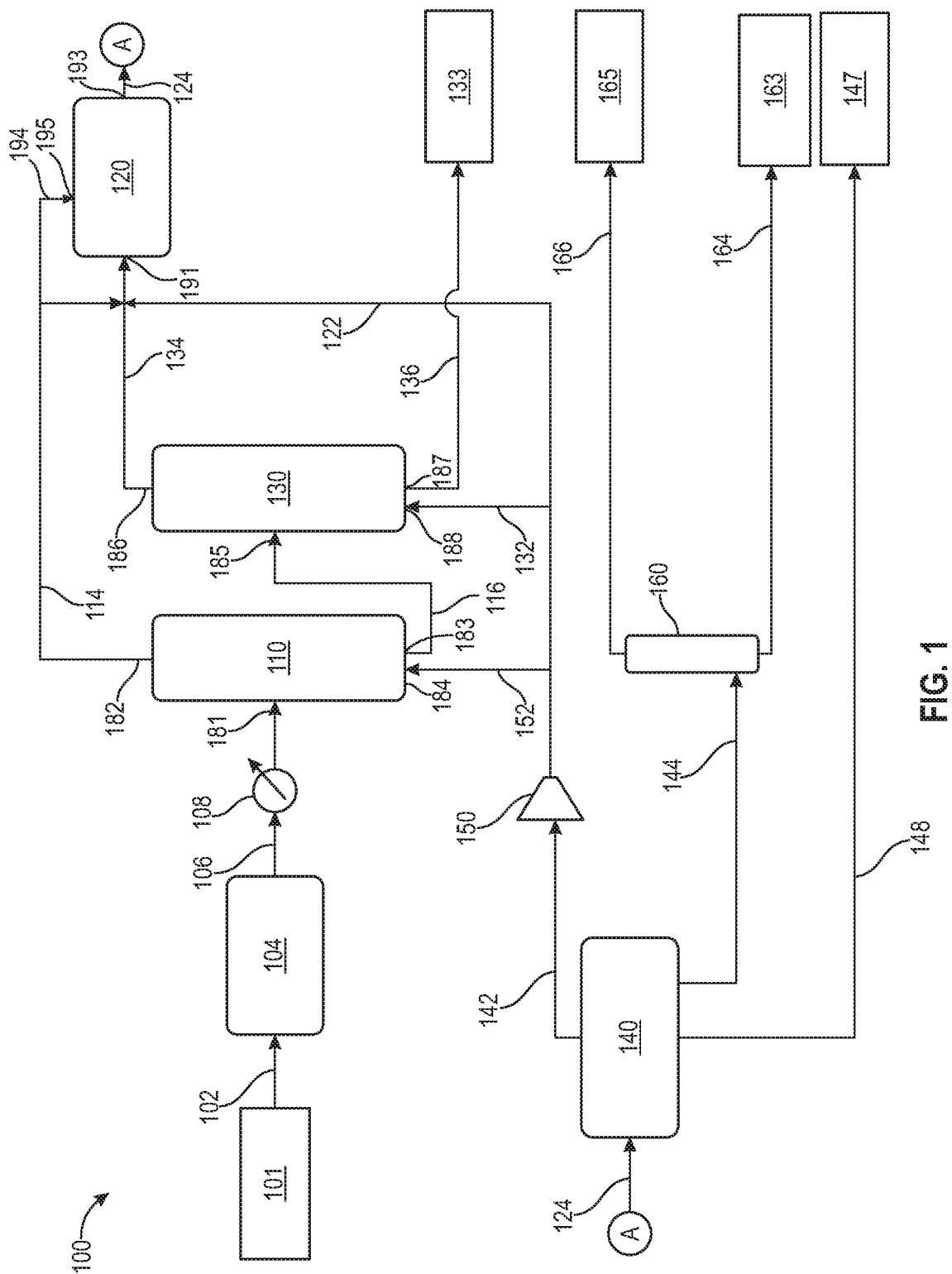
FIG. 1 shows a diagram of an apparatus demonstrating various operations that may be performed in the course of converting methanol to gasoline according to various embodiments of the present disclosure.

The present disclosure relates to methanol-to-gasoline (MTG) conversion processes and, more particularly, methanol-to-gasoline conversion processes featuring DME concentration and forward processing of unreacted methanol.

During conventional methanol-to-gasoline (MTG) conversion processes, methanol is fed to a dimethyl ether (DME) reactor, which produces an equilibrium mixture of methanol, water, and DME in the presence of a suitable catalyst. The equilibrium mixture is then fed to a methanol-to-gasoline (MTG) reactor that converts DME into gasoline using a zeolite catalyst, such as ZSM-5, to afford a mixture of gasoline hydrocarbons and light hydrocarbon gas. The water introduced to the MTG reactor may lead to catalyst deactivation and/or undesired durene formation in the gasoline hydrocarbons. Although a heavy gasoline treatment may be effective to address durene formation, doing so may significantly add to the cost of performing a MTG process.

The present disclosure provides MTG conversion processes which may aid in limiting durene formation and increasing the lifetime of the zeolite catalyst used to effect MTG conversion. Embodiments disclosed herein include removing methanol and water from the equilibrium mixture obtained from the DME reactor, thereby affording concentrated DME, prior to feeding the DME to an MTG reactor. Reducing the amount of water provided to the MTG reactor may lessen dealumination of the catalyst, thereby allowing higher reaction temperatures to be used, which may simultaneously decrease the risk of forming durene. Thus, the present disclosure may promote improved catalyst life and product quality of the gasoline hydrocarbons formed in the MTG reactor. Various implementations of the MTG conversion processes disclosed herein may involve a flow process, such as a steady flow process, or may involve a batch process.

Moreover, the methanol and water separated from the DME may be subsequently separated from one another to afford substantially water-free methanol. According to the present disclosure, the substantially water-free methanol may be forward processed and delivered to the MTG reactor, thereby providing a carbonaceous feed with a reduced water content compared to that present in the equilibrium mixture utilized in conventional MTG conversion processes. Thus, the present disclosure allows the carbonaceous feed provided within the MTG reactor to resemble the compositional makeup of the equilibrium mixture used in conventional MTG conversion processes, except for having a much lower water content. Moreover, the present disclosure allows the methanol content in the MTG reactor and the feeding location thereto to be regulated according to particular process needs, especially for the instances in which methanol aids the conversion of DME into gasoline hydrocarbons. Depending on particular process needs, some or all of the substantially water-free methanol may be forward processed to the MTG reactor. Any substantially water-free methanol not forward processed to the MTG reactor may be recycled to the DME reactor and/or delivered to a storage location for later use. Accordingly, the MTG conversion processes of the present disclosure advantageously provide a sink for the methanol formed as a result of providing concentrated DME. The processes disclosed herein also may decrease the water separation burden as a whole throughout the processes.

According to some embodiments of the present disclosure, the water and methanol may be separated from one another by gas stripping. Although any stripping gas may be used, a light hydrocarbon gas produced in the MTG reactor may be advantageously recycled to serve as the stripping gas in some embodiments of the present disclosure. Use of a recycled light hydrocarbon gas in the MTG conversion processes disclosed herein may lower the amount of exogenous material needing to be supplied to the processes, thereby lowering cost of goods. In addition, the light hydrocarbon gas brings heat from the conversion activity in the MTG reactor, and this heat may further aid the gas stripping process(es).

The light hydrocarbon gas also may be recycled to the MTG reactor and/or used as a stripping gas to promote separation of the DME in various implementations of the MTG conversion methods disclosed herein. Furthermore, the equilibrium mixture of DME may be cooled prior to the separation process (separation with or without light hydrocarbon gas) to encourage the methanol to remain with the liquid water while the more volatile DME gas is removed. Recycling of the light hydrocarbon gas to the MTG reactor may aid in controlling temperature rise therein.

Methods of the present disclosure may afford a reduced durene concentration in gasoline hydrocarbons produced during MTG conversion processes. According to various embodiments of the present disclosure, a reduced durene concentration means achieving, for example, about 2 wt. % or less durene in the product obtained from the MTG reactor. Reducing or minimizing durene formation may allow the disclosed processes to achieve ASTM gasoline specifications without the use of a Heavy Gasoline Treatment (HGT) Unit to isomerize durene, thereby lowering process operating and capital equipment costs. An example of a gasoline specification that may be achieved with the present disclosure is ASTM D-4814, "Standard Specification for Automotive Spark-Ignition Engine Fuel." Thus, a fractionation section downstream of the MTG reactor may be simplified in various embodiments of the present disclosure.

Subsequent to the MTG reactor, the gasoline hydrocarbons may undergo various additional operations, including, for example, de-ethanizing, stabilizing, splitting, and any combination thereof.

All numerical values in the present disclosure are modified by "about" or "approximately" with respect to the indicated value, and take into account experimental error and variations that would be expected by a person having ordinary skill in the art. Unless otherwise indicated, room temperature is about 25° C.

As used in the present disclosure and claims, the singular forms "a," "an," and "the" include plural forms unless the context clearly dictates otherwise. The term "and/or" as used in a phrase such as "A and/or B" herein is intended to include "A and B," "A or B," "A," and "B."

For the purposes of the present disclosure, the new numbering scheme for groups of the Periodic Table is used. In said numbering scheme, the groups (columns) are numbered sequentially from left to right from 1 through 18, excluding the f-block elements (lanthanides and actinides).

The term "hydrocarbon" refers to a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different numbers of carbon atoms. The hydrocarbons may be substituted or unsubstituted, linear or branched, cyclic or acyclic, and/or aromatic or aliphatic.

The term "light hydrocarbon gas" refers to hydrocarbon compounds that have four carbon atoms or fewer, which are gases at room temperature and atmospheric pressure. As such, light hydrocarbon gas includes compounds such as methane, ethane, propane, butane, 2-methylpropane, cyclopropane, methylcyclopropane, cyclobutane, mixtures thereof, and the like.

The term "gasoline hydrocarbons" refers to hydrocarbon compounds defined by the gasoline specification in ASTM D-4814, "Standard Specification for Automotive Spark-Ignition Engine Fuel." For example, gasoline hydrocarbons may include hydrocarbon compounds having 5 carbon atoms to 12 carbon atoms that have a vapor pressure of 35 kPa to 82.7 kPa (5.0 psi-12 psi) or higher at 37.8° C. (100° F.).

The term "substantially water-free" refers to a water concentration of about 5 wt. % water or less. As used herein, wt. % values for a product mixture at an outlet of a DME reactor account for only water, unconverted methanol, and DME, whether or not other components are present in the product mixture.

Methods for forming gasoline hydrocarbons according to the disclosure herein may comprise: providing a feed comprising methanol to a first reactor; catalytically converting at least a portion of the feed in the first reactor under dimethyl ether formation conditions in the presence of a first catalyst to form a first product mixture comprising dimethyl ether (DME), methanol, and water; separating the first product mixture into a first fraction comprising the DME and a second fraction comprising the methanol and the water; providing the first fraction to a second reactor; catalytically converting at least a portion of the DME in the second reactor under methanol-to-gasoline (MTG) conversion conditions in the presence of a second catalyst to form a second product mixture comprising gasoline hydrocarbons and light hydrocarbon gas; separating the second fraction into substantially water-free methanol and an aqueous effluent; and delivering the substantially water-free methanol to the second reactor. The substantially water-free methanol has a water content that is much lower than in conventional MTG processes. For example, recycled methanol in conventional MTG processes may exhibit a water content of up to about 25 wt. %.

Suitable conditions for the reactions of the present process are described next. The first catalyst, which is used to form DME, may include gamma-alumina, as an example. Suitable DME formation conditions in the presence of the first catalyst may include about 325° C. and 27 bar, for example. Other suitable DME formation conditions may include a temperature of about 320-330° C. and a pressure of about 25-29 bar or a temperature of about 315-335° C. and a pressure of about 20-35 bar, as examples. These temperatures and pressures may refer to those measured at the inlet of the reactor in which the reaction is conducted. Under these conditions, a DME reactor may produce an equilibrium mixture of dimethyl ether (DME), methanol, and water resulting in a conversion to 78 mol. % DME or even higher. In some examples, the conversion rate may be from 75 to 85 mol. % DME. During some operations, there may be a rise in temperature, a delta, of about 90-100° C. across the reactor (e.g., from the inlet to the outlet).

The second catalyst, which is used to form gasoline hydrocarbons in the MTG reactor, may be a zeolite catalyst or, more specifically, a crystalline aluminosilicate zeolite, such as ZSM-5, H-ZSM-5, ZSM-11, ZSM-12, ZSM-22, ZSM-23, ZSM-35, ZSM-48, and the like, and combinations thereof, as examples. Suitable MTG formation or conversion conditions in the presence of the second catalyst may include a temperature of about 325° C. and a pressure of about 22 bar, for example. Other suitable MTG conversion conditions may include a temperature of about 320-330° C. and a pressure of about 19-25 bar or a temperature of about 315-335° C. and a pressure of about 15-30 bar, as examples. Other suitable MTG conversion conditions may include a temperature in the range of 300-350° C. These temperatures and pressures may refer to those measured at the inlet of the reactor in which the reaction is conducted. During some operations, there is a rise in temperature, a delta, of about 90-100° C. across the reactor (e.g., from the inlet to the outlet). In some examples, the MTG conversion conditions employed in the present disclosure may be up to about 50° C. higher than are allowable or possible in conventional MTG processes, as a consequence of less water being present in the MTG reactor by practicing the disclosure herein.

A space velocity within the DME reactor may be about 3.0 hr$^{-1}$, referring to the capability to process a feed stream equivalent to three times the reactor volume each hour. The space velocity within the DME reactor may range from about 2.5 hr$^{-1}$ to about 3.5 hr$^{-1}$, or about 2.0 hr$^{-1}$ to about 4.0 hr$^{-1}$, or about 2.0 hr$^{-1}$ to about 4.0 hr$^{-1}$. A space velocity within the MTG reactor may be about 1.6 hr$^{-1}$, may range from about 1.4 hr$^{-1}$ to about 1.8 hr$^{-1}$, or about 1.2 hr$^{-1}$ to about 2.0 hr$^{-1}$.

The product stream from the MTG reactor may be routed to a post-MTG separation unit that operates at a "high" pressure, such as a pressure in the range of about 1379 to 1724 kPa (200-250 psig). For example, the operating pressure in the post-MTG separation unit may be 1724 kPa (250 psig). The MTG reactor, it will be understood, operates at a higher pressure than does a post-MTG separation unit.

Suitable conditions for the reactions of the MTG process may also be found in U.S. Pat. No. 9,938,205 and U.S. Patent Applications 2016/0178132, 20170121615, and 20180170823, which are incorporated herein by reference.

The embodiments of the present disclosure may comprise separating the second fraction into substantially water-free methanol and aqueous effluent by passing a stripping gas through the second fraction. The stripping gas may comprise at least a portion of the light hydrocarbon gas produced in the MTG reactor, according to various embodiments of the present disclosure.

FIG. 1 shows a diagram of apparatus 100 demonstrating various operations that may be performed in the course of converting methanol to gasoline according to various embodiments of the present disclosure. Although apparatus 100 is presented such that methanol-to-gasoline conversion is accomplished via a flow process, particularly a steady flow process, it is to be appreciated that the concepts presented herein may also be implemented as a batch process in alternative embodiments. Referring to FIG. 1, a feed stream (alternately a feed batch) comprising methanol is provided to reactor 104 from methanol supply 101 through feed line 102. The feed stream in feed line 102 may also include other substances, such as water. Reactor 104 operates under dimethyl ether formation conditions, discussed above, and contains a first catalyst that catalytically converts the methanol received from feed line 102 into dimethyl ether via a dehydration reaction to form a product mixture (equilibrium mixture) comprising dimethyl ether (DME), methanol, and water, which exits reactor 104 through line 106. After exiting reactor 104, the mixture in line 106 passes through heat exchanger 108 where it may be cooled to a lower temperature and then delivered to separation unit 110. Separation unit 110 may be a distillation column tower in various embodiments of the present disclosure. Separation unit 110 separates the product mixture from line 106 into a first fraction comprising DME as an overhead product stream in line 114 and second fraction comprising methanol and water as a bottoms stream in line 116. Thus, the concentration of DME in the first fraction in line 114 is higher than the concentration of DME in the first product mixture in line 106, which may be an equilibrium mixture of DME, methanol and water. In more specific embodiments, the first fraction in line 114 may comprise no methanol, and in other examples, the first fraction may comprise less than or equal to 10 wt. % methanol. In some specific embodiments, the first fraction in line 114 may comprise less than or equal to 5 wt. % water. In some embodiments, the first fraction in line 114 may comprise up to about 95% DME or up to about 99% DME.

Line 114 delivers the first fraction to reactor 120, which operates under MTG conversion conditions, discussed above, and contains a second catalyst capable of converting the DME into gasoline hydrocarbons. Reactor 120 may be called an MTG reactor and includes the second catalyst, which may include ZSM-5 catalyst, for example. Within reactor 120, the DME interacts with the second catalyst to form a second product mixture comprising gasoline hydrocarbons and light hydrocarbon gas, which exits as a stream through product line 124.

Referring still to FIG. 1, line 116 passes the second fraction from separation unit 110 to separation unit 130, in which methanol and water may be at least partially separated from one another. Separation unit 130 may be a distillation column tower in various embodiments of the present disclosure. Separation unit 130 separates the second fraction from line 116 into substantially water-free methanol as an overhead product stream in line 134 and an aqueous effluent 133 as a bottoms stream in line 136. Separation unit 130 may employ a stripping gas provided by stripping gas feed line 132 to promote separation of the substantially water-free methanol and aqueous effluent 133 from one another. According to particular embodiments of the present disclosure, the stripping gas within stripping gas feed line 132 may comprise a portion of the gas recycle stream separated by product separator 140, discussed below, which separates the light hydrocarbon gas formed in reactor 120. Alternately, an inert gas or a light hydrocarbon gas supplied from an external source may be supplied by stripping gas feed line 132 to promote separation of substantially water-free methanol in accordance with the disclosure above.

After being separated in separation unit 130, the substantially water-free methanol is delivered to reactor 120 via line 134. The substantially water-free methanol and the first fraction may be delivered to reactor 120 at the same location or at different locations. When delivered in the same location, the first fraction and the substantially water-free methanol may be present in a combined stream or in different streams. Thus, although not shown in FIG. 1, line 134 may merge with line 114 or may couple to reactor 120 at another port. The first fraction and the substantially water-free methanol may be delivered to reactor 120 through any combination of end inlet(s) or side inlet(s). As such, the delivery configuration shown in FIG. 1 should be considered illustrative and non-limiting. In reactor 120, the methanol may blend with the DME to participate in forming the second product mixture that subsequently exits through product line 124. The substantially water-free methanol in line 134 that reaches reactor 120 may also include stripping gas (e.g., light hydrocarbon gas) used to promote separation of the substantially water-free methanol. Optionally, the substantially water-free methanol may be condensed and separated from the stripping gas prior to being delivered to reactor 120.

Figure 2:
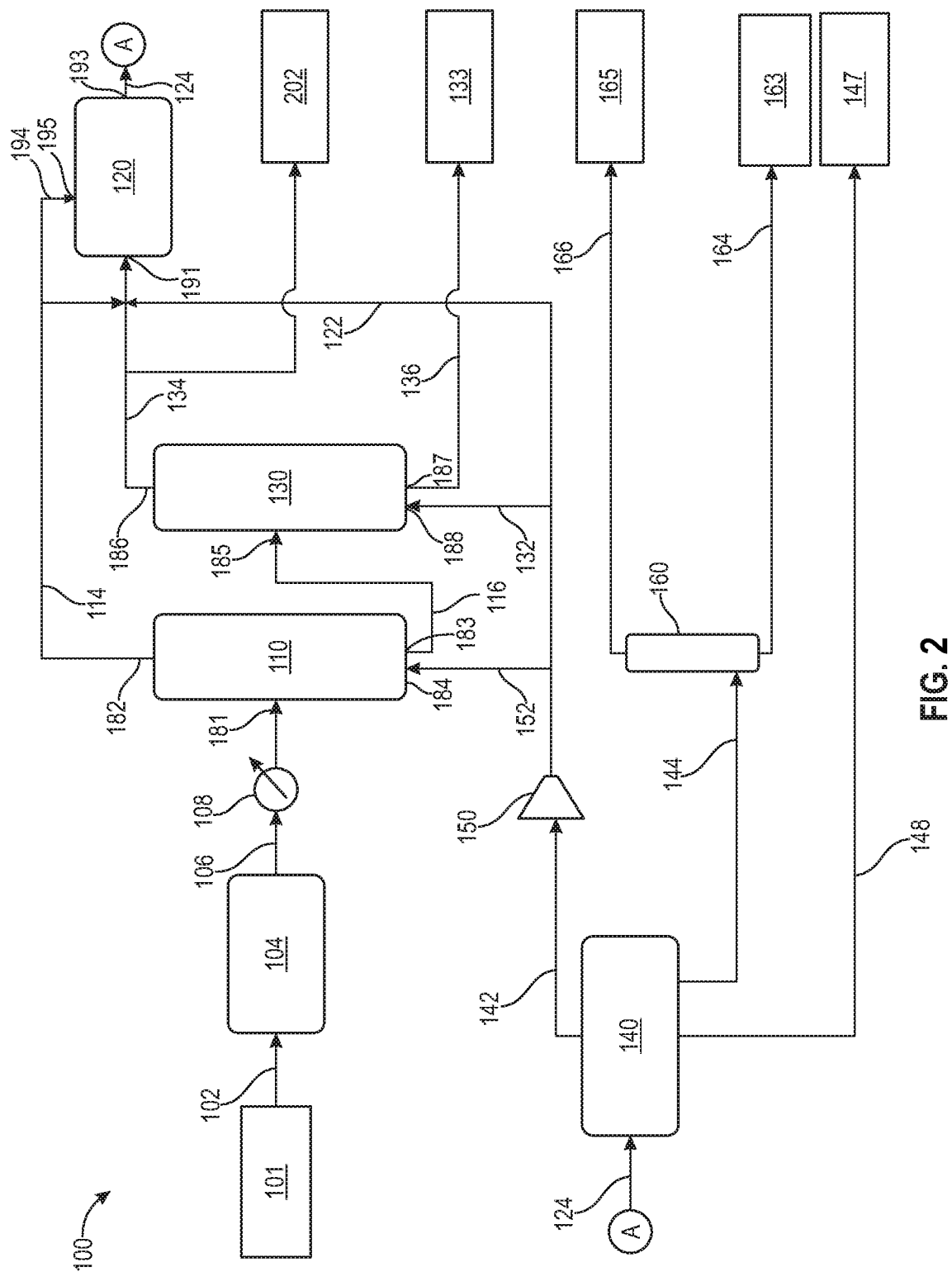
FIG. 2 shows a diagram of an alternative configuration of the apparatus of FIG. 1, demonstrating various operations that may be performed in the course of converting methanol to gasoline according to various embodiments of the present disclosure.

Alternately, as shown in FIG. 2, a portion of the substantially water-free methanol in line 134 may be routed to another process or storage location 202. For example, a portion of the substantially water-free methanol may be routed from storage location 202 to methanol supply 101 or feed line 102, or a portion of the substantially water-free methanol may be routed directly from line 134 to methanol supply 101 or feed line 102, depending on particular process needs. At least some embodiments that route the substantially water-free methanol from line 134 to methanol supply 101 may include equipment to condense and separate the methanol from an off-gas fraction before delivering the methanol to methanol supply 101. The off-gas fraction may be routed to recycle line 142 and compressor 150, if desired. Alternately, a portion of the substantially water-free methanol may be routed directly to reactor 104. Further alternately, the substantially water-free methanol may be routed entirely to the other process or storage location 202 with none being sent to reactor 120, depending upon particular process needs.

By employing separation units 110 and 130, the amount of water within reactor 120 may be decreased as compared to conventional processes in which an equilibrium mixture comprising DME is fed to an MTG reactor. Such an equilibrium mixture may exit reactor 104 through line 106 before being further processed according to the present disclosure. In contrast to conventional processes, lines 114 and 134 may supply reactor 120 with mixture of DME and methanol that includes about 5 wt. % water or less or about 1 wt. % water or less. The ratio of DME to methanol may be varied according to particular process needs. As such, the MTG reaction taking place in reactor 120 may produce less durene than would otherwise be produced at a particular temperature by feeding the equilibrium mixture directly from line 106 to reactor 120.

A slower rate of dealumination in reactor 120 may also be realized by practicing the disclosure herein. By limiting the amount of water supplied to reactor 120, reactor 120 may be operated at a higher temperature than would otherwise be possible under similar reaction conditions when greater amounts of water are present. The ability to operate reactor 120 at higher temperatures may aid in decreasing the production of durene. In various embodiments, a temperature within reactor 120 may be in the range of about 300-350° C. when applying the disclosure herein. In some examples, a temperature within reactor 120 may be in the range of about 320-330° C. Other temperatures for reactor 120 may be achievable. In at least some of these examples, the disclosed temperatures in reactor 120 pertain to inlet conditions.

Referring still to FIG. 1, the second product mixture produced in reactor 120 is delivered via product line 124 to product separator 140 where separation into light hydrocarbon gas and gasoline hydrocarbons takes place. A gas recycle stream comprising the light hydrocarbon gas exits product separator 140 via recycle line 142, and a product stream comprising gasoline hydrocarbons exits product separator 140 via line 144. Effluent 147 comprising water exits product separator 140 via discharge line 148, after which the water may be further processed or discarded. Light hydrocarbon gas in recycle line 142 may be compressed using compressor 150, such that the light hydrocarbon gas may be supplied to one or more locations upstream of product separator 140, as discussed in further detail herein.

Gasoline hydrocarbons within line 144 are delivered to debutanizer 160, where the gasoline hydrocarbons are further separated into processed gasoline 163, which exits debutanizer 160 via line 164, and into residual light hydrocarbon gas 165, including butane, which is removed from debutanizer 160 via line 166. Some process configurations may include a deethanizer, followed by a stabilizer that removes C3/C4 hydrocarbons for liquid petroleum gas (LPG) recovery. In this manner, apparatus 100 may suitably form processed gasoline 163 having acceptable quality without employing a heavy gasoline treatment (HGT). Accordingly, apparatus 100 may lack HGT capabilities in certain embodiments of the present disclosure. It is to be appreciated, however, that HGT capabilities may be present in apparatus 100 in alternative embodiments.

A gas within recycle line 122 may be delivered to reactor 120 concurrently with the first fraction from line 114 or with substantially water-free methanol from line 134 to control or limit a maximum temperature of the reaction occurring within reactor 120. Alternately, the gas may be delivered to reactor 120 at a location separate from line 114 to accomplish a similar effect (e.g., to produce a desired temperature profile in reactor 120). According to particular embodiments of the present disclosure, the gas provided to reactor 120 via recycle line 122 may comprise at least a portion of the gas recycle stream removed via recycle line 142, following compression thereof in compressor 150. Alternately, an inert gas or a light hydrocarbon gas supplied from an external source may be supplied to reactor 120 to promote temperature regulation.

The gas recycle stream in recycle line 142 may be provided to multiple locations upstream of product separator 140. In particular embodiments, a first portion of the gas recycle stream from recycle line 142 may be delivered to separation unit 130 via stripping gas feed line 132 and a second portion of the gas recycle stream may be delivered to reactor 120 via line 122, as discussed above. Optionally, and as shown in FIG. 1, a third portion of the gas recycle stream from recycle line 142 may be delivered to separation unit 110 via feed line 152 as a stripping gas to participate in or to perform separation of the first product mixture into first and second fractions, as discussed above. Some apparatus configurations do not include delivery of the third portion of the gas recycle stream to separation unit 110. The temperatures of gas recycle streams in recycle line 122, stripping gas feed line 132, and feed line 152 may differ from one another. In some embodiments, the stream in recycle line 122 is hotter than the streams in stripping gas feed line 132 and feed line 152. The gas recycle stream in recycle line 122 may be heated prior to entering reactor 120. The gas recycle streams in stripping gas feed line 132 and feed line 152 may also be heated.

Apparatus 100 may include one or more of the following features when implementing a MTG process. Separation unit 110 may be a distillation column or a separation tank that include side port 181 that serves as an inlet to receive the first product mixture in line 106, overhead port 182 that discharges the first fraction to line 114, and bottoms port 183 that discharges the second fraction to line 116. Separation unit 110 may include lower port 184 coupled to line 152 which receives the portion of stripping gas, if used, to promote separation of the first fraction and the second fraction from one another. Separation unit 130 may be a distillation column or a separation tank that includes inlet or side port 185 that receives the second fraction from line 116, overhead port 186 that discharges the substantially water-free methanol into line 134, bottoms port 187 that discharges aqueous effluent 133 into discharge line 136, and lower port 188 coupled to stripping gas feed line 132 to receive stripping gas. Reactors 104 and 120 may be fixed bed reactors, according to various embodiments of the present disclosure. In alternative embodiments, at least one of reactors 104 or 120 may be a fluidized bed reactor.

Reactor 120 may include one or more inlet ports 191 coupled to lines 114 and 134, and recycle line 122. Inlet port(s) 191 may be located at an end or a top of reactor 120, as examples, which may be referred to as an end inlet. Reactor 120 may include exit port 193 located at an end or a top of reactor 120, as examples, and coupled to line 124. In some embodiments, a portion of the DME in line 114 from separation unit 110 may be delivered from line 114 to line 194 and may be introduced to the MTG reactor through one or more side ports 195. The DME within line 194 may be used as a quench stream to control the temperature rise in MTG reactor 120. Some embodiments do not deliver DME to a side port on reactor 120.

Other embodiments of apparatus 100 may be developed based on the present disclosure. As examples, the MTG process includes adding heat to the first fraction within line 114 prior to reaching second reactor 120. Some MTG conversion processes may include adding heat to the second product mixture of product line 124 prior to reaching product separator 140.

Accordingly, some methods of the present disclosure may comprise: providing a feed stream comprising methanol to a first reactor; catalytically converting at least a portion of the feed stream in the first reactor under dimethyl ether formation conditions in the presence of a first catalyst to form a first product mixture comprising DME, methanol, and water; delivering the first product mixture in a first stream from the first reactor to a first separation unit; separating the first product mixture in the first separation unit to obtain a first fraction comprising the DME and a second fraction comprising the methanol and the water; delivering the first fraction in a second stream to a second reactor; catalytically converting at least a portion of the DME in the second reactor under MTG conversion conditions in the presence of a second catalyst to form a second product mixture comprising gasoline hydrocarbons and light hydrocarbon gas; delivering the second fraction in a third stream to a second separation unit; delivering at least a first portion of the light hydrocarbon gas to the second separation unit; separating the second fraction in the second separation unit into substantially water-free methanol and an aqueous effluent using the light hydrocarbon gas to effect stripping; and delivering the substantially water-free methanol to the second reactor.

Embodiments

A. Methods for methanol-to-gasoline conversion with forward methanol processing. The methods comprise: providing a feed comprising methanol to a first reactor; catalytically converting at least a portion of the feed in the first reactor under dimethyl ether formation conditions in the presence of a first catalyst to form a first product mixture comprising dimethyl ether (DME), methanol, and water; separating the first product mixture into a first fraction comprising the DME and a second fraction comprising the methanol and the water; providing the first fraction to a second reactor; catalytically converting at least a portion of the DME in the second reactor under methanol-to-gasoline (MTG) conversion conditions in the presence of a second catalyst to form a second product mixture comprising gasoline hydrocarbons and light hydrocarbon gas; separating the second fraction into substantially water-free methanol and an aqueous effluent; and delivering the substantially water-free methanol to the second reactor.

B. Methods for methanol-to-gasoline conversion with forward methanol processing in combination with use of a co-produced light hydrocarbon gas to effect separation of methanol. The methods comprise: providing a feed stream comprising methanol to a first reactor; catalytically converting at least a portion of the feed stream in the first reactor under dimethyl ether formation conditions in the presence of a first catalyst to form a first product mixture comprising DME, methanol, and water; delivering the first product mixture in a first stream from the first reactor to a first separation unit; separating the first product mixture in the first separation unit to obtain a first fraction comprising the DME and a second fraction comprising the methanol and the water; delivering the first fraction in a second stream to a second reactor; catalytically converting at least a portion of the DME in the second reactor under MTG conversion conditions in the presence of a second catalyst to form a second product mixture comprising gasoline hydrocarbons and light hydrocarbon gas; delivering the second fraction in a third stream to a second separation unit; delivering at least a first portion of the light hydrocarbon gas to the second separation unit; separating the second fraction in the second separation unit into substantially water-free methanol and an aqueous effluent using the light hydrocarbon gas to effect stripping; and delivering the substantially water-free methanol to the second reactor.

Embodiments A and B may have one or more of the following additional elements in any combination:

Element 1: wherein separating the second fraction into substantially water-free methanol and the aqueous effluent comprises passing a stripping gas through the second fraction.

Element 2: wherein the method further comprises separating the light hydrocarbon gas from the second product mixture.

Element 3: wherein the stripping gas comprises at least a portion of the light hydrocarbon gas formed in the second reactor.

Element 4: wherein the method further comprises cooling the first product mixture prior to separating the first product mixture into the first fraction and the second fraction.

Element 5: wherein the method further comprises delivering a first portion of the light hydrocarbon gas to the second fraction to serve as the stripping gas; and returning a second portion of the light hydrocarbon gas to the second reactor.

Element 6: wherein the method further comprises delivering a third portion of the light hydrocarbon gas to the first product mixture to aid in separating the first product mixture.

Element 7: wherein the feed is provided to the first reactor continuously as part of a flow process.

Element 8: wherein the method further comprises optionally separating the gasoline hydrocarbons from the second product mixture; and processing the gasoline hydrocarbons.

Element 9: wherein processing the gasoline hydrocarbons comprises passing the gasoline hydrocarbons through a debutanizer.

Element 10: wherein the first catalyst comprises gamma-alumina.

Element 11: wherein the second catalyst comprises a zeolite.

Element 12: wherein an amount of water in the first fraction provided to the second reactor is less than or equal to 5 wt. %.

Element 13: wherein separating the first product mixture takes place by distillation, and the DME is obtained as an overhead product from the distillation.

Element 14: wherein the first fraction and the substantially water-free methanol are delivered to the second reactor at different locations.

Element 15: wherein the first fraction and the substantially water-free methanol are delivered to the second reactor at the same location.

Element 16: wherein the method further comprises separating the light hydrocarbon gas from the second product mixture; and returning a second portion of the light hydrocarbon gas to the second reactor.

Element 17: wherein the method further comprises delivering a third portion of the light hydrocarbon gas to the first separation unit to aid in separating the first product mixture.

Element 18: wherein the method further comprises cooling the first product mixture prior to delivering the first product mixture to the first separation unit.

Element 19: wherein separating the first product mixture takes place by distillation and the DME is obtained as an overhead product from the distillation.

By way of non-limiting example, exemplary combinations applicable to A and B include: 1 and 2; 1 or 2 and 3; 1 or 2 and 4; 1 or 2 and 5; 1 or 2 and 6; 1 or 2 and 7; 1 or 2 and 8; 1 or 2 and 8 and 9; 1 or 2 and 10; 1 or 2 and 11; 1 or 2 and 12; 1 or 2 and 13; 1 or 2 and 14; 1 or 2 and 15; 1 or 2 and 16; 1 or 2 and 17; 1 or 2 and 18; 1 or 2 and 19; 3 and 4; 3 or 4 and 5; 3 or 4 and 6; 3 or 4 and 7; 3 or 4 and 8; 3 or 4 and 8 and 9; 3 or 4 and 10; 3 or 4 and 11; 3 or 4 and 12; 3 or 4 and 13; 3 or 4 and 14; 3 or 4 and 15; 3 and 4 and 16; 3 and 4 and 17; 3 and 4 and 18; 3 and 4 and 19; 5 and 6; 5 or 6 and 7; 5 or 6 and 8; 5 or 6 and 8 and 9; 5 or 6 and 10; 5 or 6 and 11; 5 or 6 and 12; 5 or 6 and 13; 5 or 6 and 14; 5 or 6 and 15; 5 or 6 and 16; 5 or 6 and 17; 5 or 6 and 18; 5 or 6 and 19; 7 and 8; 7 or 8 and 9; 7 or 8 and 10; 7 or 8 and 11; 7 or 8 and 12; 7 or 8 and 13; 7 or 8 and 14; 7 or 8 and 15; 7 or 8 and 16; 7 or 8 and 17; 7 or 8 and 18; 7 or 8 and 19; 8 and 9; 8 and 9 and 11; 8 and 9 and 12; 8 and 9 and 13; 8 and 9 and 14; 8 and 9 and 15; 8 and 9 and 16; 8 and 9 and 17; 8 and 9 and 18; 8 and 9 and 19; 10 and 11; 10 or 11 and 12; 10 or 11 and 13; 10 or 11 and 14; 10 or 11 and 15; 12 and 13; 12 or 13 and 14; 12 or 13 and 15; 10 or 11 and 16; 10 or 11 and 17; 10 or 11 and 18; 10 or 11 and 19; 14 or 15 and 16; 14 or 15 and 17; 14 or 15 and 18; 14 or 15 and 19; 16 and 17; 16 or 17 and 18; 16 or 17 and 19; and 18 and 19.

Any documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. For example, the compositions described herein may be free of any component, or composition not expressly recited or disclosed herein. Any method may lack any step not recited or disclosed herein. Likewise, the term "comprising" is considered synonymous with the term "including." Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

Unless otherwise indicated, all numbers expressing quantities of ingredients, properties such as molecular weight, process conditions, and so forth used in the present disclosure are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. For the methods herein, the order of various process steps may be rearranged in some embodiments and yet remain within the scope of the disclosure, including the claims.

One or more illustrative embodiments are presented herein. Not all features of a physical implementation are described or shown in this application for the sake of clarity. It is understood that in the development of a physical embodiment of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for one of ordinary skill in the art and having benefit of this disclosure.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to one having ordinary skill in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein.

The invention claimed is:

1. A method comprising:
   providing a feed comprising methanol to a first reactor;
   catalytically converting at least a portion of the feed in the first reactor under dimethyl ether formation conditions in the presence of a first catalyst to form a first product mixture comprising dimethyl ether (DME), methanol, and water;
   separating the first product mixture into a first fraction comprising the DME and a second fraction comprising the methanol and the water;
   providing the first fraction to a second reactor;
   catalytically converting at least a portion of the DME in the second reactor under methanol-to-gasoline (MTG) conversion conditions in the presence of a second catalyst to form a second product mixture comprising gasoline hydrocarbons and light hydrocarbon gas;
   separating the second fraction into substantially water-free methanol and an aqueous effluent, wherein separating the second fraction into substantially water-free methanol and the aqueous effluent comprises passing a stripping gas through the second fraction;
   delivering the substantially water-free methanol to the second reactor;
   delivering a first portion of the light hydrocarbon gas to the second fraction to serve as the stripping gas; and
   returning a second portion of the light hydrocarbon gas to the second reactor.

2. The method of claim 1, further comprising:
   separating the light hydrocarbon gas from the second product mixture.

3. The method of claim 1, further comprising:
   cooling the first product mixture prior to separating the first product mixture into the first fraction and the second fraction.

4. The method of claim 3, further comprising:
   delivering a third portion of the light hydrocarbon gas to the first product mixture to aid in separating the first product mixture.

5. The method of claim 1, wherein the feed is provided to the first reactor continuously as part of a flow process.

6. The method of claim 1, further comprising:
   optionally separating the gasoline hydrocarbons from the second product mixture; and
   processing the gasoline hydrocarbons,
   wherein processing the gasoline hydrocarbons comprises passing the gasoline hydrocarbons through a debutanizer.

7. The method of claim 1, wherein the first catalyst comprises gamma-alumina.

8. The method of claim 1, wherein the second catalyst comprises a zeolite.

9. The method of claim 1, wherein an amount of water in the first fraction provided to the second reactor is less than or equal to 5 wt. %.

10. The method of claim 1, wherein separating the first product mixture takes place by distillation and the DME is obtained as an overhead product from the distillation.

11. The method of claim 1, wherein the first fraction and the substantially water-free methanol are delivered to the second reactor at different locations.

12. The method of claim 1, wherein the first fraction and the substantially water-free methanol are delivered to the second reactor at the same location.

13. A method comprising:
providing a feed stream comprising methanol to a first reactor;
catalytically converting at least a portion of the feed stream in the first reactor under dimethyl ether formation conditions in the presence of a first catalyst to form a first product mixture comprising DME, methanol, and water;
delivering the first product mixture in a first stream from the first reactor to a first separation unit;
separating the first product mixture in the first separation unit to obtain a first fraction comprising the DME and a second fraction comprising the methanol and the water;
delivering the first fraction in a second stream to a second reactor;
catalytically converting at least a portion of the DME in the second reactor under MTG conversion conditions in the presence of a second catalyst to form a second product mixture comprising gasoline hydrocarbons and light hydrocarbon gas;
delivering the second fraction in a third stream to a second separation unit;
delivering at least a first portion of the light hydrocarbon gas to the second separation unit;
separating the second fraction in the second separation unit into substantially water-free methanol and an aqueous effluent using the light hydrocarbon gas to effect stripping;
delivering the substantially water-free methanol to the second reactor; and
optionally separating the gasoline hydrocarbons from the second product mixture; and processing the gasoline hydrocarbons,
wherein processing the gasoline hydrocarbons comprises passing the gasoline hydrocarbons through a debutanizer.

14. The method of claim 13, further comprising:
separating the light hydrocarbon gas from the second product mixture; and
returning a second portion of the light hydrocarbon gas to the second reactor.

15. The method of claim 14, further comprising:
delivering a third portion of the light hydrocarbon gas to the first separation unit to aid in separating the first product mixture.

16. The method of claim 13, further comprising:
cooling the first product mixture prior to delivering the first product mixture to the first separation unit.

17. The method of claim 13, wherein separating the first product mixture takes place by distillation and the DME is obtained as an overhead product from the distillation.

18. The method of claim 13, wherein the first fraction and the substantially water-free methanol are delivered to the second reactor at different locations.

19. The method of claim 13, wherein the first fraction and the substantially water-free methanol are delivered to the second reactor at the same location.

* * * * *